United States Patent [19]  [11] 4,180,467
Barth  [45] Dec. 25, 1979

[54] STABLE DENTURE SOAK PRODUCT

[75] Inventor: Jordan B. Barth, East Brunswick, N.J.

[73] Assignee: Colgate-Palmolive Company, New York, N.Y.

[21] Appl. No.: 650,600

[22] Filed: Jan. 20, 1976

Related U.S. Application Data

[63] Continuation of Ser. No. 441,588, Feb. 11, 1974, abandoned, which is a continuation of Ser. No. 187,524, Oct. 7, 1971, abandoned, which is a continuation of Ser. No. 829,133, May 29, 1969, abandoned.

[51] Int. Cl.$^2$ .......................... A61K 7/20; C11D 7/18
[52] U.S. Cl. ......................................... 252/99; 252/95; 252/100; 252/157; 252/186; 424/44; 424/53; 424/55

[58] Field of Search ..................... 252/350, 95, 96, 99, 252/186, 157, 100; 424/44, 53, 55, 48

[56] References Cited

U.S. PATENT DOCUMENTS 3,518,343  6/1970  Welsh .................................. 252/350

Primary Examiner—Benjamin R. Padgett
Assistant Examiner—Deborah L. Kyle
Attorney, Agent, or Firm—Norman Blumenkopf; Herbert S. Sylvester; Murray M. Grill

[57] ABSTRACT

This disclosure relates to effervescent denture soak compositions having stability and sustained effervescence comprising an acid anhydride, a solid organic acid, a solid inorganic carbonate and oxidizing agents. The acid anhydride reduces caking tendencies by acting as an internal dessicant and increase the effervescence time ($CO_2$ evolution).

3 Claims, No Drawings

STABLE DENTURE SOAK PRODUCT

This is a continuation, of application Ser. No. 441,588 filed Feb. 11, 1974, now abandoned which is a continuation of U.S.S.N. 187,524 filed Oct. 7, 1971, abandoned which in turn is a continuation of U.S.S.N. 829,133 filed May 29, 1971 abandoned.

The present invention relates to a stable denture soak composition having sustained effervescence.

The art is replete with effervescent denture soak formulae; some of which contain oxidizing agents as the source of effervescence, others comprising a carbonate as the source of carbon dioxide liberation, and still others utilizing both an oxidizing agent and carbonation agents (a carbonate plus an acid capable of reacting to release carbon dioxide) in a single composition. One of the problems encountered with these formulations is their lack of stability, largely due to the hygroscopic nature of the ingredients. This well-recognized problem has been solved in the past by coating the active ingredients with an inert material prior to compounding. However, this solution has not been completely satisfactory because of the added expense entailed in its manufacture, since additional process steps as well as ingredients are necessary.

Another problem encountered by the prior art denture soak products is the lack of sustained effervescence which is desirable to effect complete cleansing of the dentures as well as act as an indicator of the completion of said cleansing action.

Accordingly, it is an object of this invention to overcome both of the aforementioned problems and provide a stable denture soak product having sustained effervescence.

It has now been found that an improved denture soak product having both increased stability against caking productive of sustained effervescence when dissolved in water, can be formulated by the addition of a solid acid anhydride to a composition comprising oxidizing agents, an inorganic carbonate and an organic acid. The inorganic carbonate reacts with both the organic acid and the acid anhydride (after conversion to acid form) to release carbon dioxide which effervesces in an aqueous medium. The solid organic acid and the solid inorganic carbonate usually completes effervescing ($CO_2$ release) within one to two minutes after being dissolved in water, whereas the acid anhydride slowly hydrolyzes (30 minutes is required at 70° F.) to the acid and then reacts with the carbonate to produce the $CO_2$. The solid acid is necessary to initiate the $CO_2$ evolution, and the anhydride continues to produce $CO_2$ for 30 minutes at 70° F. via a time lag in the conversion of the anhydride to the acid, thereby giving sustained effervescence. The anhydride also reduces caking tendencies of the composition by acting as an internal dessicant and preventing premature evolution of $CO_2$.

More specifically this invention relates to a stable, water-soluble solid composition with sustained effervescence and of substantially acid to neutral pH when dissolved in an aqueous solution comprising at least one solid water-soluble oxidizing agent, a solid water-soluble carbonate compound, a solid water-soluble organic acid and a solid water-soluble acid anhydride.

The acid anhydrides utilized herein are nontoxic, solid, water-soluble inorganic or organic and capable of hydrolyzing and subsequently reacting with the inorganic carbonate to evolve $CO_2$. Specific examples of acid anhydride include boric anhydride, succinic anhydride, adipic anhydride, fumaric anhydride, tartaric anhydride, citric anhydride, malic anhydride, maleic anhydride and the like. The acid anhydride content may vary from about 1–60% and preferably from 5–10% by weight of the total composition.

The source of carbon dioxide is a water-soluble alkali-metal carbonate compound selected from the group consisting of sodium bicarbonate, sodium carbonate, sodium sesquicarbonate, potassium carbonate, potassium bicarbonate, and mixtures thereof, which reacts with a solid organic acid selected from the class consisting of tartaric acid, citric acid, malic acid, maleic acid, fumaric acid, succinic acid, etc. and mixtures thereof, in the presence of water to produce effervescence (bubbles). The carbonate content may range from 5% to 75%, by weight, and preferably from 35% to 50%; the acid content may vary from about 5% to 50% by weight, and preferably from about 15% to 25% by weight of the total composition. In many systems maximum effervescence level is attained when 3 parts carbonate to 2 parts acid concentration is utilized.

The oxidizing agents offer another source of effervescence (liberation of molecular oxygen) and are preferably the persalts such as the alkali metal perborates, persulfates, percarbonates, perphosphates and the like. The simple addition of these water-soluble peroxygen compounds to water produces a highly effective source of active oxygen which is particularly useful in oxidation reactions, thereby providing considerable improvements in applications where peroxygen compounds are employed such as for antiseptic, cleansing and bleaching activity. The degree of active oxygen liberation relates to both the volume and speed and is dependent on the particular peroxygen compound employed. For example, sodium perborate monohydrate has three times as much active oxygen as potassium persulfate, but the latter has a stronger oxidation potential (stronger oxidizing agent). Consequently, it is preferred to use a mixture of persalts in order to obtain the combined advantages of both oxidizing agents. The total amount of oxidizing agents utilized herein may vary from 5–50% and preferably 20–40% by weight of the total composition, the distribution between the various agents being dependent on the desired end result. More specifically, a composition having less active oxygen but yielding stronger oxidizing action will utilize a greater amount of the persulfate salt, whereas a formulation requiring a greater and quick release of active oxygen will employ a greater amount of the perborate. Other suitable solid per-oxygen compounds include ammonium persulfate, sodium persulfate, sodium pyrophosphate peroxide, sodium carbonate peroxide, etc., The denture soak composition may also contain any suitable surface-active or detersive material to enhance its cleansing activity. Suitable detergents are water-soluble, non-toxic salts of higher fatty acid monoglyceride, monosulfate, higher alkyl sulfate, alkyl aryl sulfonate, higher alkyl sulfoacetate, higher fatty acid ester of 1, 2 dihydroxy propane sulfonate, higher fatty acid amides of taurine and and higher fatty acid esters of isothionic acid; the substantially saturated higher aliphatic acyl amides of lower aliphatic amino carboxylic acid compounds, such as those having 12 to 16 carbons in the acyl radical, and the like. Examples of such amides are N-lauroyl, myristoyl or palmitoyl sarcosides. The various surface-active materials should be used in a suitable amount such as up to about 5%, preferably from about 0.1 to 5% by weight of the denture soak preparation.

The effervescent denture soak composition may contain certain water-soluble dyes which act as timing indicators by turning colorless at the completion of the cleansing action. The initial coloration of the dye, upon dissolution of the dry composition in water, is bleached out in a period of time approximating the time required for cleaning the denture. The type and amount of dye selected is dependent on the desired completion time of the cleansing activity as well as on the composition and pH of the denture product. It has been found that a period of at least 10-15 minutes and up to 30 minutes is a desirable cleansing time. Accordingly, at substantially neutral pH, the azo dyes have been found particularly desirable due to their ability to be readily oxidized to a colorless state in the required time. A specific example of an azo dye is acid red #14 (Ext D and C Red #10) which is the disodium salt of 2-(4-sulfo-1-naphthylazo) 1-naphthol-4-sulfonic acid. Other dyes with suitable fading times are FD and C Blue #2, FD and C Green #1, FD and C Green #2, FD and C Violet #1, D and C Yellow #10, Ext D and C Violet #2 and Ext D and C Yellow #3. The amount of dye incorporated in the composition may vary from about 0.005% to 0.5% and preferably from 0.01% to 0.04% by weight of the total.

Various other adjuvant materials may also be incorporated in the present denture soak preparations. Minor amounts of flavor oils such as oils of spearmint, peppermint and wintergreen may be included to impart a mild and pleasant flavor and odor to the cleaned denture. However, when adding a flavor oil (oil to about 1.0%), it has been found desirable to also incorporate minor amounts (e.g. 1 to 5%) of a flavor retainer or carrier such as magnesium carbonate to avoid the separation of the oil droplets from the rest of the dry composition. Other flavor retainers may be utilized provided they readily absorb the flavor oils and prevent flavor weeping. Minor amounts of other suitable water-soluble additives may be included such as sweetners, foam depressants, preservatives, buffers, fillers, diluents, binders, etc., provided they do not adversely affect the properties and characteristics of the denture soak product.

The denture cleansing compositions of the instant invention are dry, water-soluble powders or granules which may be packaged in bulk in assorted containers or in individual premeasured packets. The product may also be marketed in the form of tablets. It is preferable that the aforesaid product completely dissolve in water to yield a clear solution having a substantially neutral pH, at which both carbon dioxide and active oxygen become readily available, thereby providing the effervescence and oxidation required for the proper cleansing of dentures. An alkaline solution has the disadvantage of hastening the corrosion of metal parts of the dentures, whereas acid solutions tend to etch the dentures.

The term denture includes all kinds of orthodontic appliances such as false teeth, removable dental plates and bridges, artificial teeth and the like.

The following specific examples are further illustrative of the nature of the present invention, but it is to be understood that the invention is not limited thereto. The compositions are prepared in the usual manner as indicated, and all amounts of the various ingredients are by weight unless otherwise specified.

EXAMPLE I

| Ingredients | % by Weight |
|---|---|
| Citric acid | 16.50 |
| Sodium bicarbonate | 34.14 |
| Acid Red #14 | 0.01 |
| Succinic anhydride | 5.00 |
| Potassium persulfate (KH SO$_5$) | 28.00 |
| Sodium perborate (Na BO$_2$ H$_2$O$_2$) | 15.00 |
| Sodium salt of dodecyl benzene sulfonate | 0.10 |
| Magnesium carbonate | 1.00 |
| Flavor oils | 0.25 |

The above ingredients are thoroughly mixed and blended to produce a homogeneous powdered mixture which is stable. A denture is immersed in a dilute aqueous solution of this compositon which has a neutral pH. After about 15 minutes of soaking, during which time the solution continuously effervesces and the red color fades, the denture is bright, clean and odorless.

EXAMPLE II

The succinic anhydride of Example I is increased to 10% and the citric content is reduced to 11.50%. The stable powdered mixture yields a clear solution when dissolved in water for the cleansing of dentures.

EXAMPLE III

| Ingredients | % by Weight |
|---|---|
| Malic acid | 16.50 |
| Succinic anhydride | 5.00 |
| Na H CO$_3$ | 35.14 |
| Na BO$_2$ H$_2$O$_2$ | 15.00 |
| KH SO$_5$ | 28.00 |
| Acid Red #14 | .01 |
| Sodium salt of dodecyl benzene sulfonate | 9.10 |
| Flavor oils | 0.25 |

The malic acid, succinic anhydride, Na H CO$_3$, Na BO$_2$ H$_2$O$_2$, KH SO$_5$, flavor oils and the dye are thoroughly blended. The sodium salt of alkyl benzene sulfonate is added to and thoroughly mixed with the above ingredients to obtain a homogeneous mixture. A denture treated herewith as described in Example I is bright, clean and odorless.

EXAMPLE IV

In the preparation of tablets, 2% sodium benzoate is added and blended with the formulation of Example III in order to act as a lubricant in the tableting process.

EXAMPLE V

The dodecyl benzene sulfonate sodium salt content of Example III was increased to 0.8% in order to lubricate the mixture for tableting.

Example VI

| Ingredients | % by Weight |
|---|---|
| Malic acid | 19.27 |
| Boric anhydride | 5.00 |
| Na H CO$_3$ | 45.00 |
| KH SO$_5$ | 18.67 |
| Na BO$_2$ H$_2$O$_2$ | 10.00 |
| Methyl naphthalene sodium sulfonate | 1.60 |
| Alkyl pheroxypoly (ethyleneoxy) ethanol | 0.20 |
| Acid Red #14 | 0.01 |
| Flavor oils | 0.20 |

The above powdered ingredients are thoroughly mixed to yield a stable denture soak product.

EXAMPLE VII

Maleic anhydride is substituted for the boric anhydride of Example VI, yielding a stable denture soak formulation.

Although the present invention has been described with reference to particular embodiments and examples, it will be apparent to those skilled in the art that variations and modifications of this invention can be made and that equivalents can be substituted therefor without departing from the principles and true spirit of the invention.

What is desired to be claimed is:

1. A stable water-soluble solid composition with sustained carbon dioxide effervescence and of substantially neutral pH when dissolved in an aqueous solution consisting essentially of 20 to 43% by weight of at least one solid water-soluble inorganic peroxygen salt, 35 to 50% by weight of sodium or potassium bicarbonate compound, 15 to 25% by weight of a solid water-soluble organic acid selected from the group consisting of tartaric, citric, malic, maleic, fumaric and succinic acids and 5 to 10% by weight of a solid water-soluble acid anhydride capable of hydrolyzing and reacting with the said carbonate to evolve carbon dioxide when said composition is dissolved in water and selected from the group consisting of boric, succinic, adipic, fumaric, tartaric, citric, malic and maleic anhydrides.

2. A composition in accordance with claim 1 wherein said water-soluble inorganic peroxygen salt is a mixture of potassium persulfate and sodium perborate, said bicarbonate compound is sodium bicarbonate and the weight ratio of bicarbonate to acid ranges from about 3:2 to 3:1.

3. A composition according to claim 2 wherein said weight ratio is at least about 2:1.

* * * * *